(12) United States Patent
Guala (10) Patent No.: US 10,918,851 B2
(45) Date of Patent: Feb. 16, 2021

(54) VALVE CONNECTOR FOR MEDICAL LINES

(71) Applicant: Industrie Borla S.p.A., Moncalieri (IT)

(72) Inventor: Gianni Guala, Turin (IT)

(73) Assignee: INDUSTRIE BORLA S.P.A., Turin (IT)

(*) Notice: Subject to any disclaimer, the term of this patent is extended or adjusted under 35 U.S.C. 154(b) by 50 days.

(21) Appl. No.: 15/745,362

(22) PCT Filed: Aug. 4, 2016

(86) PCT No.: PCT/IB2016/054716
§ 371 (c)(1),
(2) Date: Jan. 16, 2018

(87) PCT Pub. No.: WO2017/021927
PCT Pub. Date: Feb. 9, 2017

(65) Prior Publication Data
US 2018/0200502 A1    Jul. 19, 2018

(30) Foreign Application Priority Data

Aug. 5, 2015  (IT) .................. 102015000042421

(51) Int. Cl.
*A61M 39/26* (2006.01)
*A61M 39/10* (2006.01)
*A61M 39/04* (2006.01)

(52) U.S. Cl.
CPC .......... *A61M 39/26* (2013.01); *A61M 39/045* (2013.01); *A61M 2039/1033* (2013.01); *A61M 2039/1077* (2013.01); *A61M 2039/267* (2013.01)

(58) Field of Classification Search
CPC ................. A61M 39/06; A61M 39/45; A61M 2039/1033; A61M 2039/267; A61M 2039/1066; A61M 2039/1077
See application file for complete search history.

(56) References Cited

U.S. PATENT DOCUMENTS

| 2010/0234798 A1* | 9/2010 | Huang | A61M 39/26 |
|---|---|---|---|
| | | | 604/68 |
| 2011/0282302 A1* | 11/2011 | Lopez | A61M 39/16 |
| | | | 604/247 |

(Continued)

FOREIGN PATENT DOCUMENTS

| EP | 1834665 A1 | 9/2007 |
|---|---|---|
| EP | 2123322 A2 | 11/2009 |

(Continued)

OTHER PUBLICATIONS

Patent Cooperation Treaty, Notification of Transmittal of the International Search Report and the Written Opinion of the International Searching Authority, or the Declaration for PCT/IB2016/054716 dated Oct. 10, 2016, 12 pages.

(Continued)

*Primary Examiner* — Manuel A Mendez
*Assistant Examiner* — Justin L Zamory
(74) *Attorney, Agent, or Firm* — Heslin Rothenberg Farley & Mesiti P.C.; Victor Cardona (57) ABSTRACT

A valve connector for infusion medical lines includes an outer tubular body, an inner hollow spike and an intermediate sealing member formed by an elastic hollow element including a head with a pre-slit normally closed. The elastic hollow element has a base part substantially generally barrel-shaped and a wall having a differentiated radial thickness.

1 Claim, 7 Drawing Sheets

(56) References Cited

U.S. PATENT DOCUMENTS

2013/0197453 A1   8/2013  Yeh
2015/0297830 A1*  10/2015 Okiyama .............. A61M 5/162
                                                          604/250

FOREIGN PATENT DOCUMENTS

| | | |
|---|---|---|
| EP | 2881138 A1 | 6/2015 |
| FR | 3001393 A1 | 8/2014 |
| JP | 2001505102 A | 4/2001 |
| JP | 2001522657 A | 11/2001 |
| JP | 2011500103 A | 1/2011 |
| JP | 2014030489 A | 2/2014 |
| WO | 9822178 A1 | 5/1998 |
| WO | 2008052140 A2 | 5/2008 |
| WO | 2014074929 A1 | 5/2014 |

OTHER PUBLICATIONS

Office Action from corresponding Japanese application dated Dec. 17, 2019.

\* cited by examiner

FIG. 1

PRIOR ART

FIG. 2

PRIOR ART

VALVE CONNECTOR FOR MEDICAL LINES

CROSS REFERENCE TO RELATED APPLICATIONS

This application is a national stage filing under section 371 of International Application No. PCT/IB2016/054716, filed on Aug. 4, 2016, published in English on Feb. 9, 2017, as WO2017/021927 A1 and which claims priority to Italian Application No. 102015000042421, filed on Aug. 5, 2015, the entire disclosure of these applications being hereby incorporated herein by reference.

FIELD OF THE INVENTION

The present invention regards valve connectors for medical lines, for example infusion lines by means of a fluid substance introducer, typically made of a Luer connector or Luer-Lock for example of a needleless syringe.

STATE OF THE PRIOR ART

Document EP-1834665A1 by the same Applicant discloses a valve connector according to the preamble of claim 1, comprising a tubular body having an inlet end provided for the engagement of a fluid introducer and an outlet end. A hollow spike is arranged axially in the cavity of the tubular body and it has a closed tip facing the inlet end thereof, while it is in communication with the outlet end thereof. The connector further includes an elastic sealing member formed by an elastic hollow element interposed between the tubular body and the hollow spike and having an elastic head provided with a pre-slit and normally arranged in a closing condition in the inlet end of the tubular body, in which the pre-slit is closed. The elastic head can be displaced axially against the closed tip of the hollow spike to interact therewith assuming an elastically deformed condition to open the pre-slit. The elastic hollow element further comprises a base part radially spaced from the hollow spike so as to define an annular chamber therewith.

In this known connector, the base part has a generally cylindrical axial wall which constitutes an elastic thrust member which tends to keep the head of the sealing member in the aforementioned closing condition. During the axial displacement of the elastic head from the closing condition to the opening condition, the wall of this base part bends elastically in the aforementioned annular chamber.

This connector according to the aforementioned document EP-1834665A1, is easy to clean and disinfect ("swabbable") on the side of the inlet end, and satisfactorily meets several requirements crucial to use thereof in the medical industry: in particular, an efficient sealed closure of the inlet end of the tubular body, so as to guarantee a total antibacterial barrier, even after repeatedly opening and closing the valve connector.

An improvement of this connector is described and illustrated in document EP-2123322A1, also belonging to the same Applicant, with the aim of improving the airtight sealing of the connector in the operative condition thereof, i.e. in the condition elastically deformed by the elastic hollow element of the sealing member even in case of high internal overpressure. For such purpose, the valve connector according to EP-2123322A1 provides for a substantially inextensible containment annular member and it is axially slidable in the tubular body of the connector due to the displacement of the elastic head between the closing and opening conditions. This ring guarantees the airtight sealing of the connector in the operative condition thereof even in case of generation of high pressure therein: however, the presence thereof creates some challenges and complications in the mechanised connector manufacturing and assembly process, and the thus giving rise to increase of costs.

Thus, the Applicant sought to address the technical problem of attaining a functionally similar effect but eliminating the problem related to providing the connector with the aforementioned ring.

According to the invention, this object is attained thanks to the fact that the base part of the elastic hollow element is generally substantially barrel-shaped with a wall having a differentiated radial thickness and externally formed with thickened axial lobes whose radial thickness progressively decreases towards axial areas of minimum thickness of said wall.

Thanks to this configuration, it was surprisingly observed that the airtight sealing of the connector in the operative condition thereof is also guaranteed even with internal pressure similar to the one borne by the ring-equipped connector according to the aforementioned EP-2123322A1, but without manufacturing complications and relative assembly challenges arising from the presence of the containment ring. It is deemed that this result may come from the fact that the peculiar configuration of the base part of the elastic hollow element requires, in the opening condition of the connector, an equally peculiar elastic deformation in the annular chamber delimited between the elastic hollow element and the hollow spike due to which the portion of such elastic hollow element that extends towards the head with pre-slit is firmly fastened against the corresponding portion of the hollow spike.

BRIEF DESCRIPTION OF THE DRAWINGS

The invention will now be described in detail, purely by way of non-limiting example, with reference to the attached drawings, wherein.

DETAILED DESCRIPTION OF THE INVENTION

Figure 1:
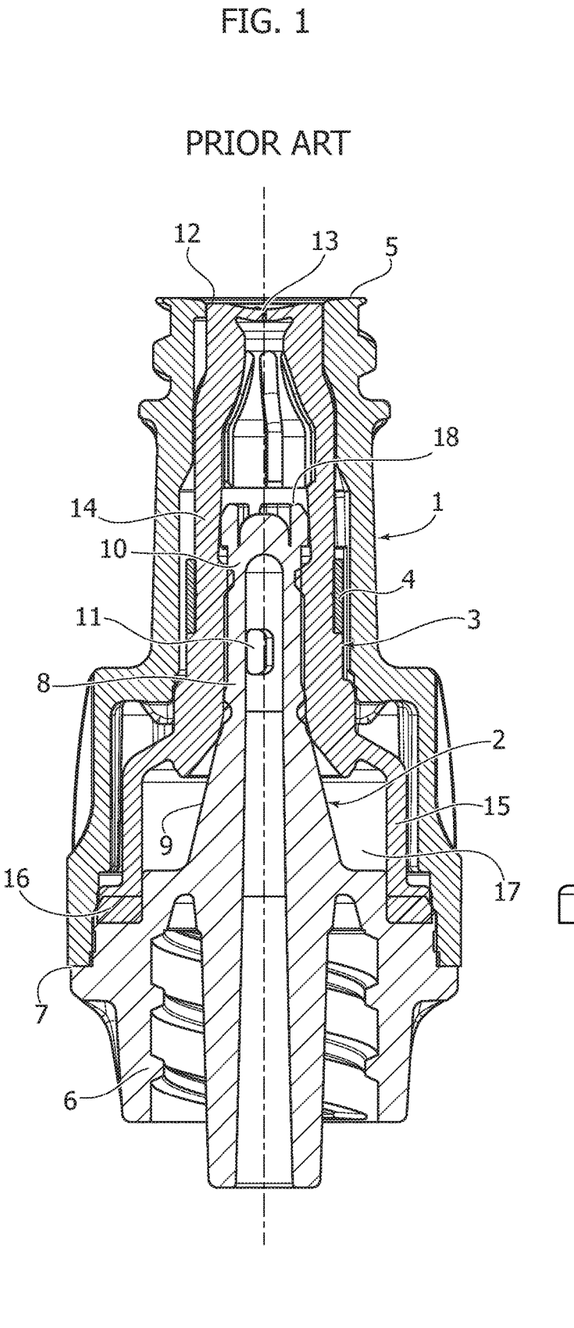
FIG. 1 is an axial section schematic view of a valve connector according to the prior art addressed previously.

FIG. 1 shows a sectional view of the valve connector according to the prior art document EP-2123322A1 addressed previously. It essentially comprises four components: an outer tubular body 1, an inner hollow spike 2 coaxially arranged in the cavity of the tubular body 1, an elastic sealing member indicated in its entirety with 3, and an annular member 4. Typically, the tubular body 1, the hollow spike 2 and the ring 4 are made of rigid plastic material, while the sealing member 3 is made of an elastic material, silicone rubber for example.

The tubular body 1 has an inlet end 5 shaped to form a female Luer-lock connection member for engagement, in a conventional fashion, with a male Luer-lock connection member of a fluid introducer, constituted by a needleless syringe for example.

The hollow spike 2 has a base part 6 shaped to form a male Luer-lock connection member, or of any other type, permanently joined in 7 to the end of the tubular body 1 opposite to the inlet end 5 thereof. On the base side 6 there integrally projects a tubular pin 8 having an initial portion with a conical outer surface 9 followed by a cylindrical portion 10 formed with at least one through hole 11 and whose free end consists in a closed tip 18 facing the inlet end 5 of the tubular body 1, at a given distance therefrom.

The sealing member 3 comprises, in a single piece, an elastic head 12 having a central pre-slit 13, a generally cylindrical intermediate portion 14 and a base part 15 terminating with an annular flange 16 axially locked between the base 6 of the hollow spike 2 and the hollow body 1.

Figure 2:
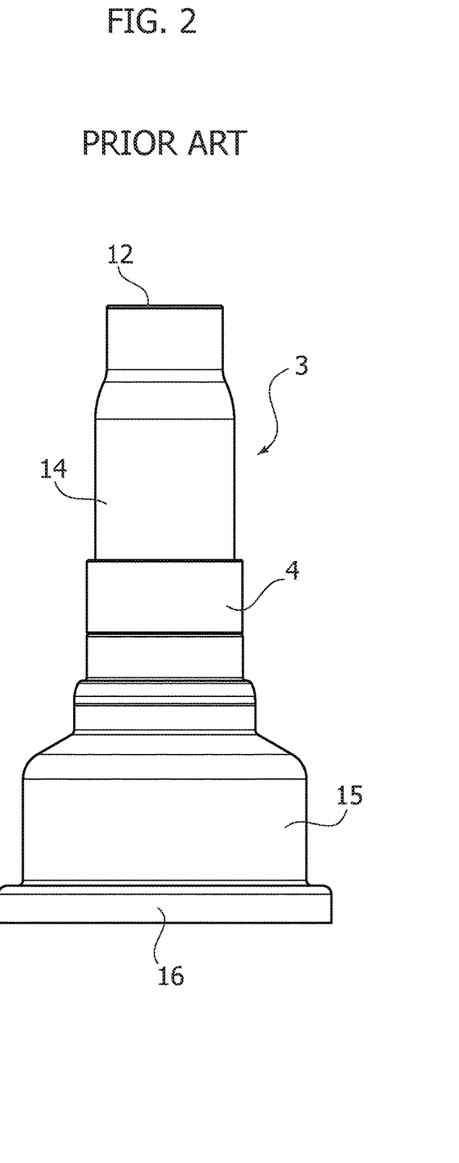
FIG. 2 is a perspective view and in larger scale of a component of the connector according to the prior art of FIG. 1.

In the condition of closing the elastic head 12 in the inlet end 5 of the hollow body 1, the pre-slit 13 is kept fastened and closed, thus obtaining an anti-bacterial protection barrier between the interior of the valve connector and the external. In such condition the cylindrical intermediate part 14 of the elastic hollow element 3 is at sealing contact with the cylindrical portion 10 of the hollow spike 2 on sides opposite to the hole 11, and the base part 15 thereof has a substantially cylindrical undeformed configuration, also better observable in FIG. 2. The base part 15 delimits an annular chamber 17 with the conical surface portion 9 of the hollow spike 2.

The containment ring 4 is inextensible and surrounds a part of the cylindrical intermediate portion 14 of the elastic hollow element 3 so as to hold it fastened, in the operative condition of the connector even in the presence of high internal pressure, against the cylindrical portion 10 of the hollow spike 2 thus guaranteeing an airtight sealing on opposite sides with respect to the through opening 11.

In use, when the fluid introducer is engaged through the inlet opening 5 of the tubular body 1, the elastic head 12 is axially pushed towards the internal of the connector thanks to the elastic deformation of the base part 15, which bends in the annular chamber 17. When the elastic head 12 interacts with the closed tip 18 of the hollow spike 2, the pre-slit 13 is opened thus allowing the passage of flow from the introducer to the base connector 6 of the hollow spike 2, through the hole 11 thus placed in communication with the inlet end 5 of the tubular body 1.

Figure 3:
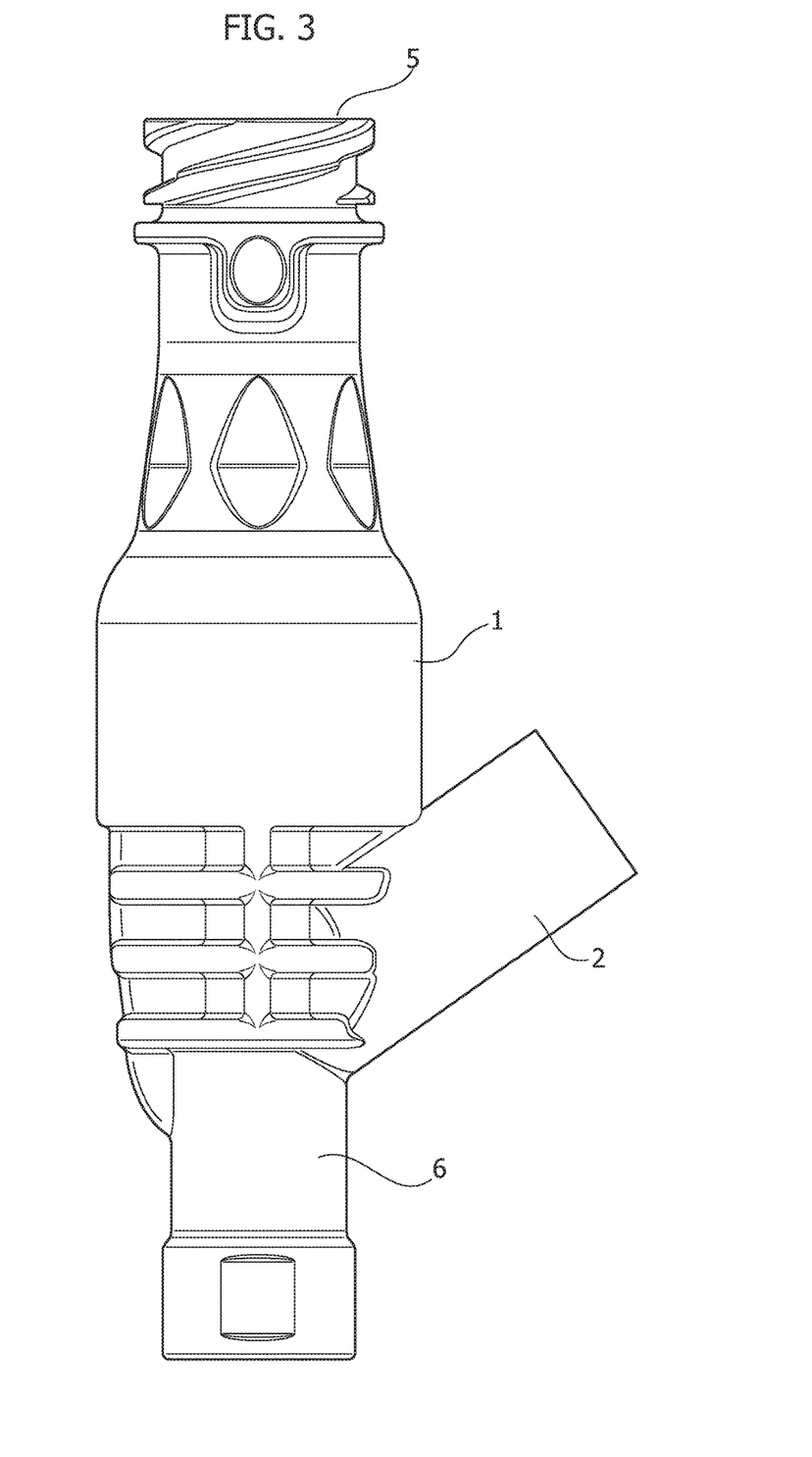
FIG. 3 is an elevational view of an embodiment of the calve connector according to the invention.
Figure 4:
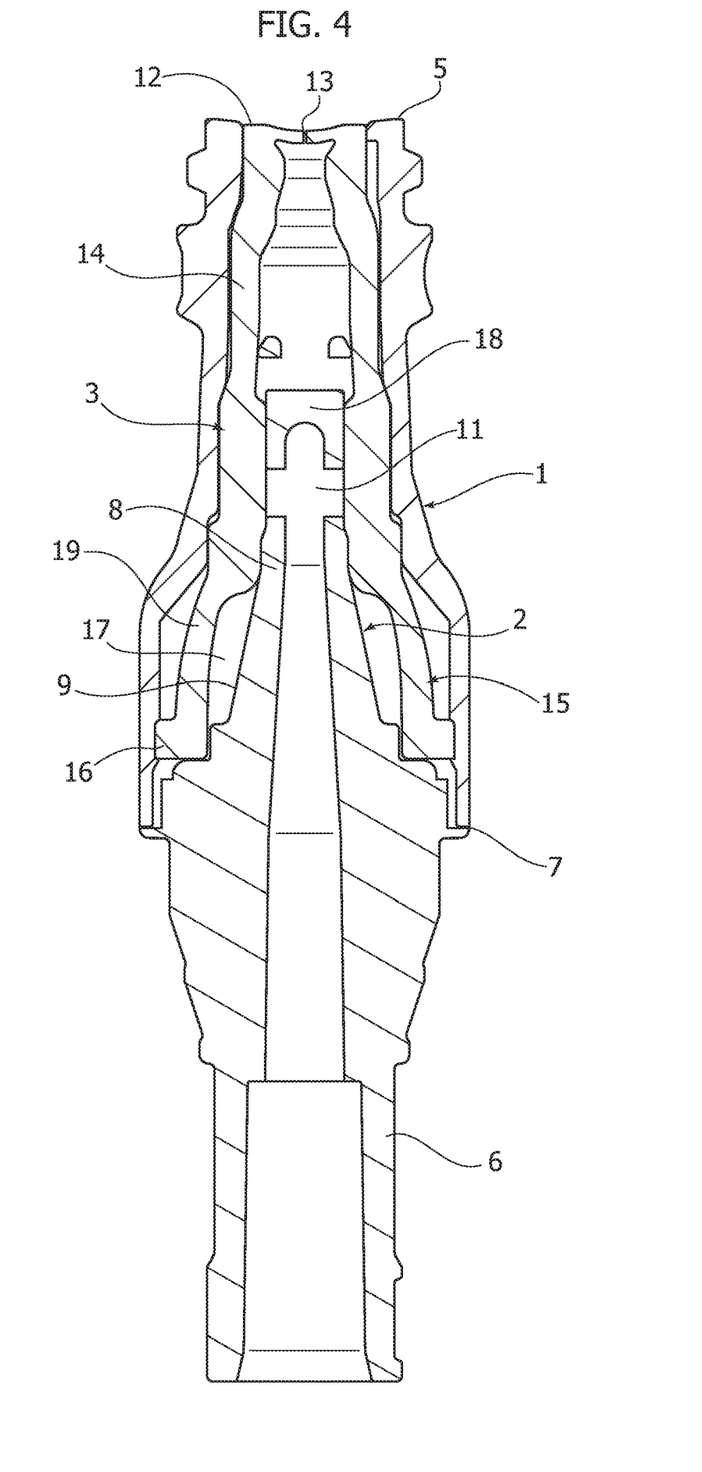
FIG. 4 is an axial sectional view of FIG. 3.
Figure 5:
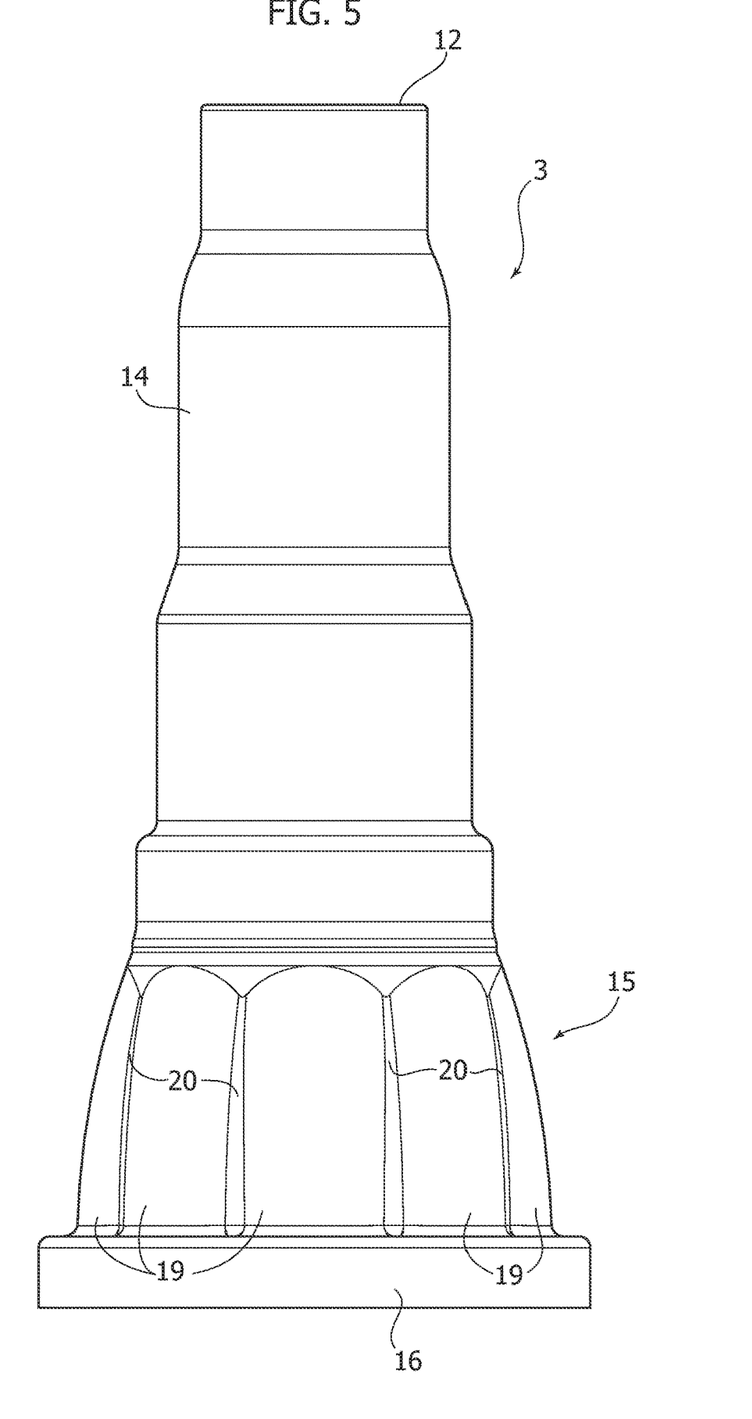
FIG. 5 is an elevational view and in larger scale of a component of the valve connector according of FIG. 3.

The general configuration and operation of the valve connector according to the invention represented in FIGS. 3 and 4 are similar to the ones described previously with reference to FIGS. 1 and 2, and only the differences will be described in detail using the same reference numbers for the identical or similar parts.

The valve connector according to the invention, as represented in the example, consists in a so-called "Y" fitting, whose outer body 1 defines a main duct in communication with a secondary lateral duct 2. It should be observed that the valve connector according to the invention could have a general configuration entirely similar to the one represented in FIGS. 1 and 2, i.e. without the secondary duct 2.

Figure 6:
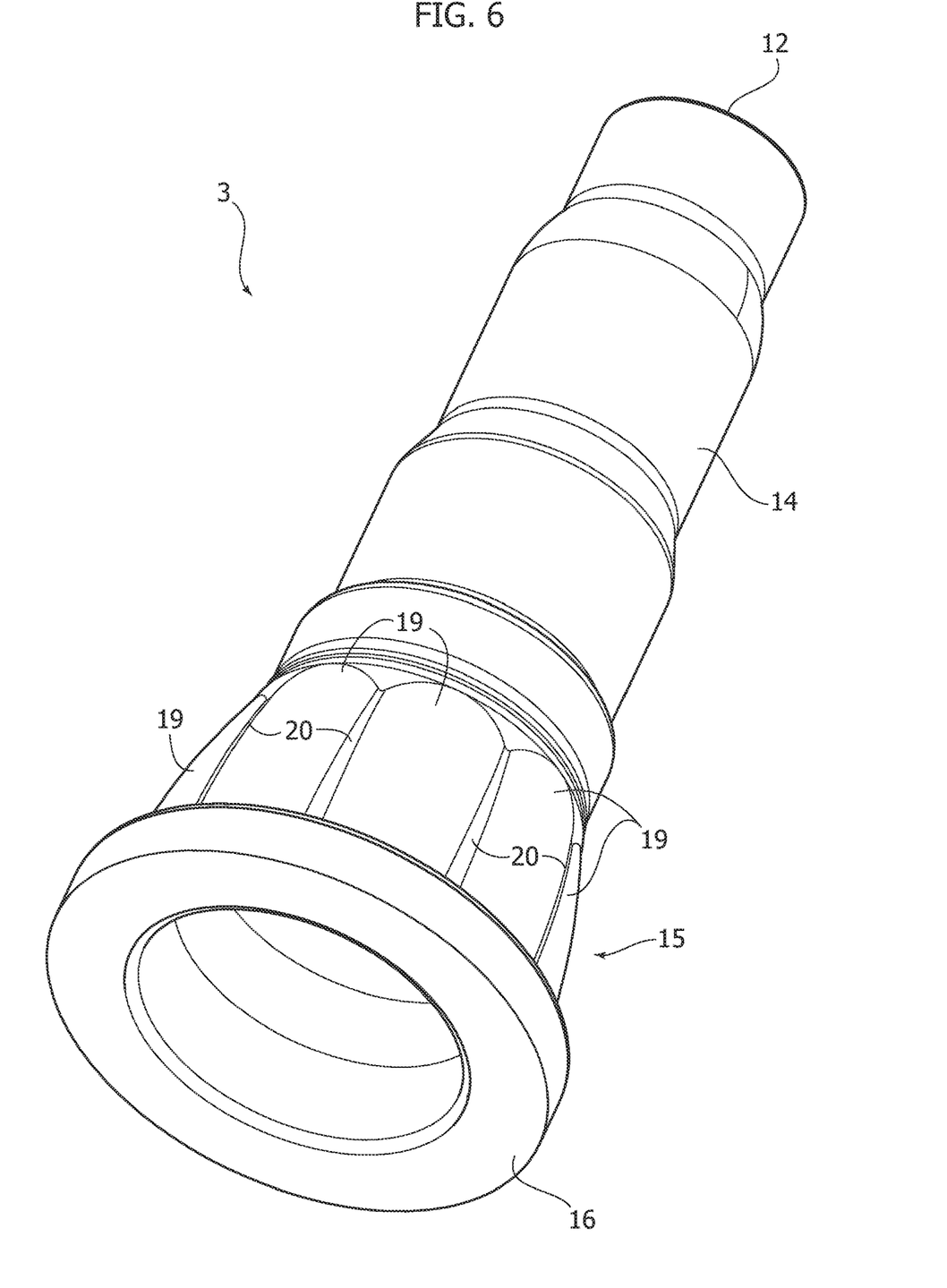
FIG. 6 is a perspective view of FIG. 5.
Figure 7:
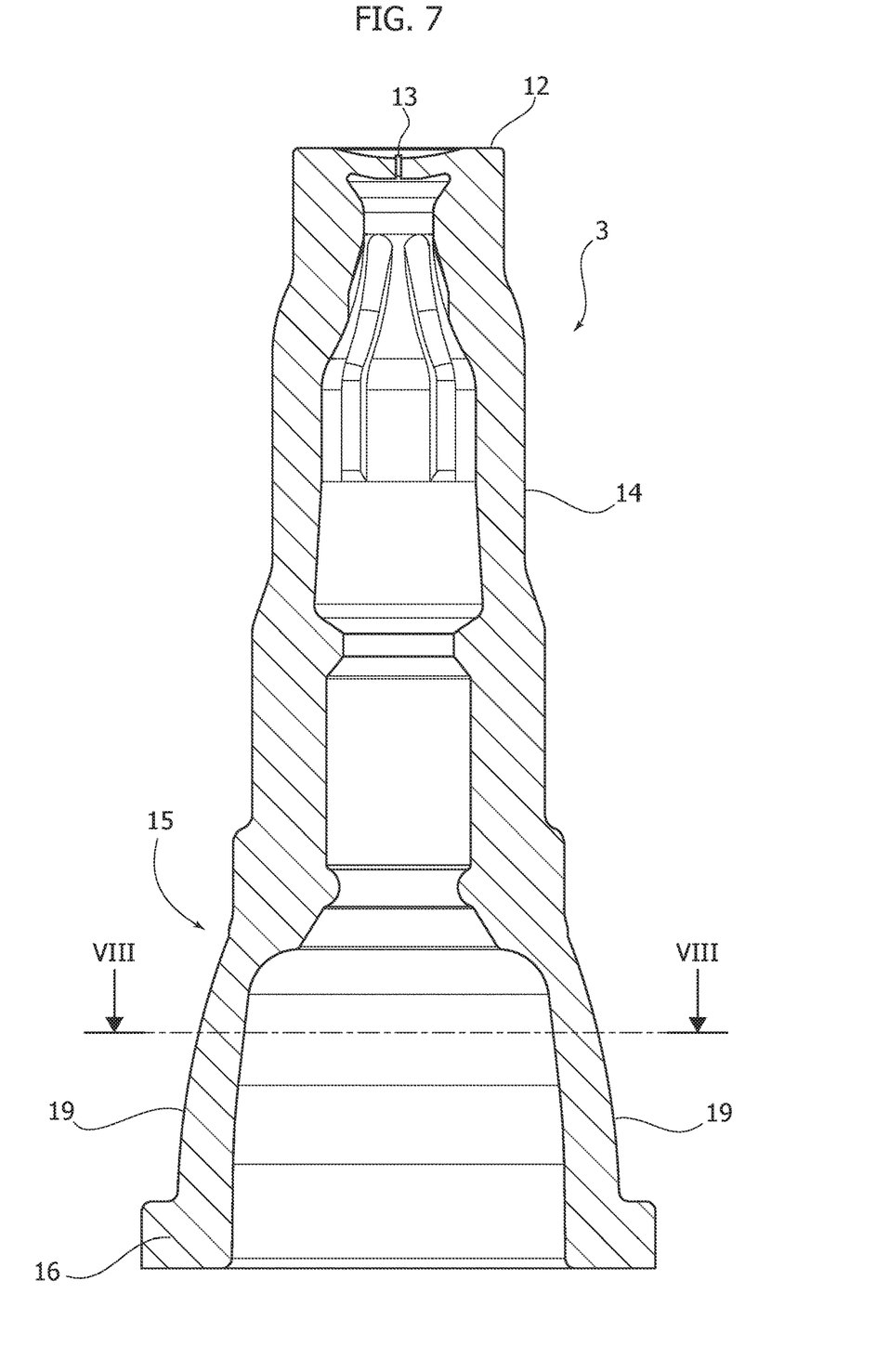
FIG. 7 is an axial sectional view of FIG. 5.
Figure 8:
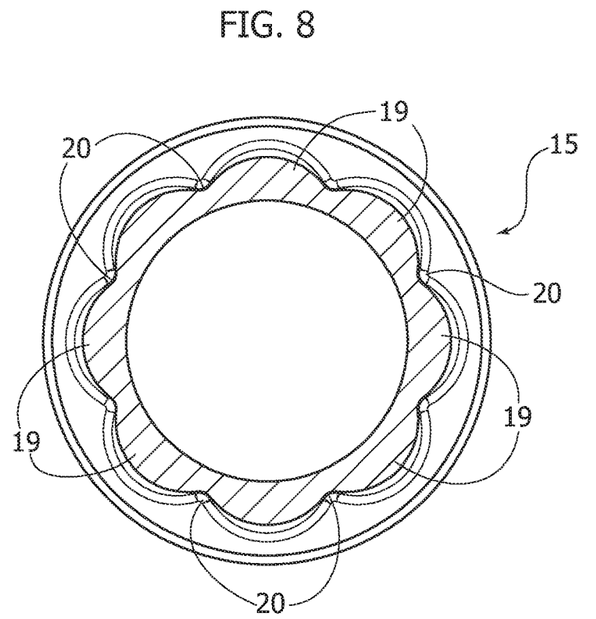
FIG. 8 is a cross-sectional view according to line VIII-VIII of FIG. 7.
Figure 9:
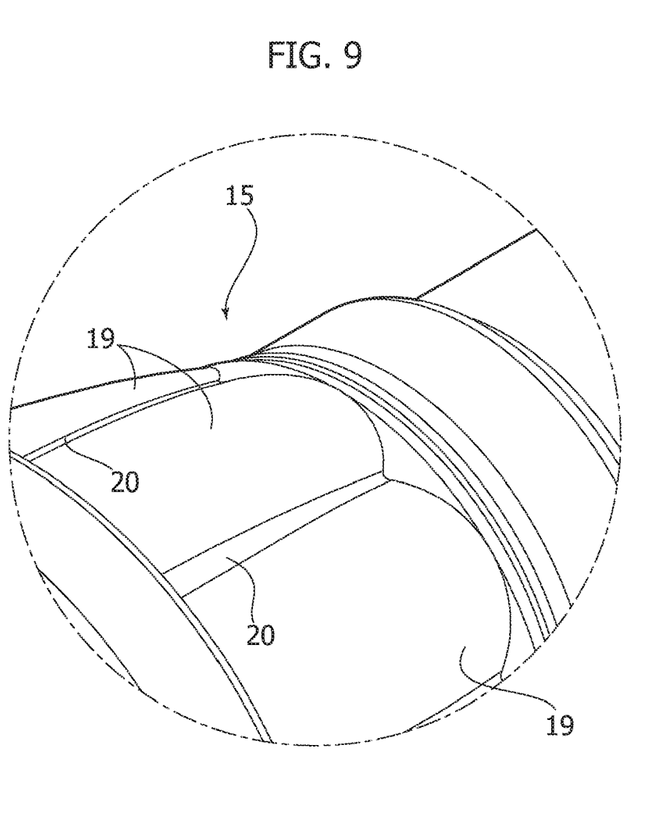
FIG. 9 is a perspective view and in larger scale of a detail of FIG. 6.

The only actual conceptual and distinctive difference of the valve connector according to the invention with respect to the previously described prior art lies in the absence of the containment ring indicated previously with reference number 4, and in a different configuration of the base part 15 of the elastic hollow element 3 comprised between the cylindrical portion 14 thereof and the end flange 16. As illustrated further in detail in FIGS. 5 to 8 the base part 15 has a substantially general barrel-like shape with differentiated radial thickness instead of a cylindrical section with constant section. As even more clearly observable in FIG. 6 and in FIGS. 8 and 9 such base part 15 is externally formed with thickened axial lobes 19 whose radial thickness is maximum at the centre and progressively decreases towards axial areas of minimum thickness 20 of the wall of the base part 15.

Thanks to this distinctive configuration, it was surprisingly observed that the behaviour of the elastic hollow element 15, and thus of the valve connector as whole, is entirely similar—as concerns sealing in the operative condition thereof—to that of the known connector provided with the containment ring 4, even in case of high internal pressure. It is deemed that this is due to the fact that, when the elastic hollow element 3 is elastically deformed due to the insertion of the fluid introducer into the valve connector and the ensuing opening of the pre-slit 13, the base portion 15 of the elastic hollow element 3 bends in the annular chamber 17 analogously to the case of the connector according to the prior art, but the barrel-like configuration thereof with lobes as previously described acts, deforming, so as to surprisingly fasten the cylindrical portion 14 of such elastic hollow element 3 against the corresponding cylindrical portion 8 of the hollow spike 2, albeit the absence of the containment ring 4. Thus, this allows obtaining a functional result similar to that of the valve connector described previously with reference to the prior art, but obtained in a simpler and more economic fashion in particular as regards the assembly of the valve connector.

In addition, such configuration advantageously allows reducing the overall radial dimensions of the valve connector.

Obviously, the construction details and the embodiments may widely vary with respect to what has been described and illustrated, without departing from the scope of protection of the invention, as defined in the claims that follow.

The invention claimed is:

1. Valve connector for medical lines, comprising:
   a tubular body having an inlet end designed for the engagement of a fluid introducer and an outlet end,
   a hollow spike arranged axially within the cavity of the tubular body and having a closed tip facing said inlet end of the tubular body and axially spaced therefrom, said hollow spike being in communication with said outlet end,
   a sealing member formed by an elastic hollow element interposed between said tubular body and said hollow spike and having an elastic head provided with a pre-slit and normally arranged in a closure condition in said inlet end of the tubular body, wherein said pre-slit is closed;
   said elastic head being axially moveable against said closed tip of the hollow spike for interacting with said closed tip so as to take an elastically deformed condition of opening of said pre-slit, and
   said elastic hollow element further comprising a base part radially spaced from said hollow spike so as to define therewith an annular chamber,
   said base part of the elastic hollow element having a generally barrel-like shape with a wall having a differentiated radial thickness and formed externally with thickened axial lobes, each lobe of said axial lobes having a radial thickness progressively decreasing towards axial areas having minimum thicknesses of said wall, said axial lobes arranged circumferentially adjacent to each other on said base part, and each axial area of said axial areas having minimum thicknesses located circumferentially between a plurality of said axial lobes, said elastic hollow element comprising a first cylindrical portion and said hollow spike comprising a second cylindrical portion, said elastic hollow element elastically deformable in response to an insertion of the fluid introducer into the inlet end such that said axial lobes bend in the annular chamber to fasten the first cylindrical portion against the second cylindrical portion.

\* \* \* \* \*